US012667527B2

(12) United States Patent
Wu et al.

(10) Patent No.: US 12,667,527 B2
(45) Date of Patent: Jun. 30, 2026

(54) COMPOSITION FOR CARING FOR KERATIN MATERIALS

(71) Applicant: L'OREAL, Paris (FR)

(72) Inventors: Xiaoming Wu, Shanghai (CN); Xiuxia Wang, Shanghai (CN)

(73) Assignee: L'OREAL, Paris (FR)

( * ) Notice: Subject to any disclaimer, the term of this patent is extended or adjusted under 35 U.S.C. 154(b) by 544 days.

(21) Appl. No.: 18/251,959

(22) PCT Filed: Dec. 22, 2020

(86) PCT No.: PCT/CN2020/138315
§ 371 (c)(1),
(2) Date: May 5, 2023

(87) PCT Pub. No.: WO2022/133728
PCT Pub. Date: Jun. 30, 2022

(65) Prior Publication Data

US 2024/0009090 A1 Jan. 11, 2024

(51) Int. Cl.

| | |
|---|---|
| ***A61K 8/06*** | (2006.01) |
| ***A61K 8/34*** | (2006.01) |
| ***A61K 8/60*** | (2006.01) |
| ***A61K 8/81*** | (2006.01) |
| ***A61K 8/892*** | (2006.01) |
| ***A61Q 19/08*** | (2006.01) |

(52) U.S. Cl.
CPC ................ *A61K 8/062* (2013.01); *A61K 8/34* (2013.01); *A61K 8/345* (2013.01); *A61K 8/602* (2013.01); *A61K 8/817* (2013.01); *A61K 8/8176* (2013.01); *A61K 8/8188* (2013.01); *A61K 8/892* (2013.01); *A61Q 19/08* (2013.01)

(58) Field of Classification Search
CPC .......... A61K 8/062; A61K 8/34; A61K 8/345; A61K 8/602; A61K 8/817; A61K 8/8176; A61K 8/8188; A61K 8/892; A61Q 19/08
USPC ........................................................... 514/25
See application file for complete search history.

(56) References Cited

U.S. PATENT DOCUMENTS

| | | | | |
|---|---|---|---|---|
| 8,445,459 | B2 | 5/2013 | Laboureau et al. | |
| 8,883,125 | B2 | 11/2014 | Allemand et al. | |
| 8,926,996 | B2 * | 1/2015 | Yoshimura ............... | A61K 8/86 424/59 |
| 9,237,998 | B2 | 1/2016 | Chiou et al. | |
| 10,064,791 | B2 | 9/2018 | Plismy Juquel et al. | |
| 2008/0003191 | A1 | 1/2008 | Simonnet et al. | |
| 2010/0168055 | A1 | 7/2010 | Laboureau et al. | |
| 2014/0050679 | A1 | 2/2014 | Allemand et al. | |
| 2015/0174047 | A1 | 6/2015 | Chiou et al. | |
| 2015/0313810 | A1 | 11/2015 | Plismy Juquel | |
| 2016/0120788 | A1 * | 5/2016 | Brun ........................ | A61K 8/19 424/401 |

FOREIGN PATENT DOCUMENTS

| | | | |
|---|---|---|---|
| CN | 1213293 | A | 4/1999 |
| CN | 111067832 | A | 4/2020 |
| FR | 3 059 546 | A1 | 6/2018 |
| JP | H06271421 | A * | 9/1994 |
| JP | 2008-13559 | A | 1/2008 |
| JP | 2009-541476 | A | 11/2009 |
| JP | 2019-533688 | A | 11/2019 |
| KR | 10-2019-0073467 | A | 6/2019 |
| WO | WO 2020/120704 | A1 | 6/2020 |
| WO | WO 2020/132860 | A1 | 7/2020 |

OTHER PUBLICATIONS

Combined Chinese Office Action and Search Report issued Apr. 30, 2024 in Chinese Patent Application No. 202080108084.4 (with English translation of Category of Cited Documents), 8 pages.
Japanese Office Action issued Feb. 12, 2025 in Japanese Patent Application No. 2023-535754 (with English translation), 12 pages.
Anonymous, "The Regenerating Brightening Cream Mask", MINTEL, Database GNPD [Online] , Database accession No. 8169985, Oct. 7, 2020, XP093220816, 4 pages.
Anonymous, "Revitalizing Eye Cream", MINTEL, Database GNPD [Online], Database accession No. 6399375, Mar. 11, 2019, XP093220820, 7 pages.
Extended European Search Report issued Nov. 25, 2024 in European Patent Application No. 20966309.5, 8 pages.

(Continued)

*Primary Examiner* — Yih-Horng Shiao
(74) *Attorney, Agent, or Firm* — Oblon, McClelland, Maier & Neustadt, L.L.P.

(57) ABSTRACT

A composition for caring for keratin materials in the form of an oil-in-water cream comprising: (i) from 3% to 10.5% by weight of at least one cosmetic active compound of formula (I), relative to the total weight of the composition: (I) wherein R1, R2 and R3 are, independently from each other, selected from H, —OH, —$CH_2$OH and —$CH_2$CH(OH)$CH_3$; (ii) at least one water-soluble or water-dispersible copolymer derived from 2-acrylamidomethyl propanesulfonic acid and a nonionic water-soluble comonomer (AMPS copolymer); (iii) at least one silicone compound; and (iv) ethanol. A non-therapeutic method for caring for keratin materials, comprising applying said composition to the keratin materials.

(I)

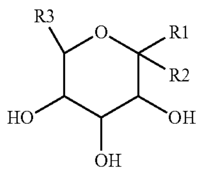

13 Claims, No Drawings

(56) References Cited

OTHER PUBLICATIONS

International Search Report & Written Opinion issued on Sep. 26, 2021 in PCT/CN2020/138315 filed on Dec. 22, 2020, 12 pages.
Office Action issued Sep. 30, 2025, in corresponding Korean Patent Application No. 10-2023-7017331, 7 pages.

* cited by examiner

COMPOSITION FOR CARING FOR KERATIN MATERIALS

TECHNICAL FIELD

The present invention relates to a cosmetic composition. In particular, the present invention relates to a composition for caring for keratin materials. The present invention also relates to a non-therapeutic method for caring for keratin materials.

BACKGROUND ART

The skin is the protective barrier for the human body. It protects the interior of the body from physical injury (such as trauma) and biological injury (such as bacteria, viruses or fungi). The epidermis is a keratinized stratified pavimentous epithelium. Its mean thickness ranges from 60 to 100 μm and may reach 600 to 700 μm on the sole of the feet and the palm of the hands. It consists mainly of keratinocytes, but also other cells, and rests on a basal membrane that separates it from the dermis.

During the menopause, the skin undergoes changes in all its compartments, i.e. dermal and epidermal.

The main changes concern the dermis and are a decrease in the collagen content and in the thickness of the dermis. In menopausal women, this results in thinning of the skin and/or of the mucous membranes. Women then experience a sensation of "dry skin" or of taut skin and an accentuation of the surface wrinkles and fine lines is observed. The skin has a rough feel. Finally, the skin shows decreased suppleness.

The main changes concerning the epidermis are a decrease in keratinocyte differentiation, resulting in a deficit in the proteins matrix of the cornified cell, an increase in metalloproteinases, which are proteases that degrade the extracellular matrix and that participate in ageing of the skin, and also a decrease in the synthesis of various glycosaminoglycans.

The development of formulations dedicated to caring for and/or making up the skin and/or lips, is permanent.

A wide variety of cosmetic compositions have been used to care for the skin, for example, to combat the ageing of the skin. There is a commercial product for antiaging of the skin comprising proxylane, which presents a very sticky sensory to the skin if the concentration of proxylane is relatively high. Consumers feel an unappealing greasy after application of such a product. Thus, such a product is still not satisfying.

There is thus still a need to formulate a composition for caring for the skin, which comprises proxylane or the like at a relative high concentration without sticky sensory.

Besides, the composition is expected to have a relatively high consistency as a cream.

SUMMARY OF THE INVENTION

The Applicant has now discovered that it is possible to formulate such compositions having the desired properties as described above.

Specifically, the applicant has discovered that it is possible to formulate compositions for caring for keratin materials, which comprises proxylane or the like at a relative high concentration, meanwhile it has a relatively high consistency as a cream without sticky sensory.

Accordingly, in a first aspect, the present invention provides a composition for caring for keratin materials in the form of an oil-in-water cream comprising:

(i) from 3% to 10.5% by weight of at least one cosmetic active compound of formula (I), relative to the total weight of the composition:

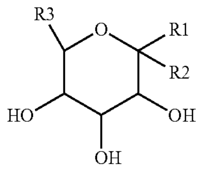

(I)

wherein R1, R2 and R3 are, independently from each other, selected from H, —OH, —$CH_2OH$ and —$CH_2CH(OH)CH_3$;

(ii) at least one water-soluble or water-dispersible copolymer derived from 2-acrylamidomethyl propanesulfonic acid and a nonionic water-soluble comonomer (AMPS copolymer);

(iii) at least one silicone compound; and (iv) ethanol.

The composition of the present invention is in the form of an oil-in-water cream. Thus, said composition comprises a continuous aqueous phase and a dispersed oily phase.

In a second aspect, the present invention provides a non-therapeutic method for caring for keratin materials, comprising applying the composition according to the first aspect of the present invention to the keratin materials.

The composition of the present invention can deliver an antiaging effect to the keratin materials without sticky sensory.

In addition, the composition according to the present invention is stable at 4° C., room temperature (25° C.), and 45° C.

Furthermore, the composition according to the present invention has a relatively high viscosity, a smooth and fine texture as a cream and has a good spreadability.

Other advantages of the present invention will emerge more clearly on reading the description and the examples that follow.

DETAILED DESCRIPTION OF THE INVENTION

Unless otherwise defined, all technical and scientific terms used herein have the same meaning as commonly understood by those skilled in the art the present invention belongs to. When the definition of a term in the present description conflicts with the meaning as commonly understood by those skilled in the art the present invention belongs to, the definition described herein shall apply.

In that which follows and unless otherwise indicated, the limits of a range of values are included within this range, in particular in the expressions "between . . . and . . . " and "ranging from . . . to . . . ".

Moreover, the expression "at least one" used in the present description is equivalent to the expression "one or more".

Throughout the instant application, the term "comprising" is to be interpreted as encompassing all specifically mentioned features as well optional, additional, unspecified ones. As used herein, the use of the term "comprising" also discloses the embodiment wherein no features other than the specifically mentioned features are present (i.e. "consisting of").

Unless otherwise specified, all numerical values expressing amount of ingredients and the like which are used in the description and claims are to be understood as being modified by the term "about". Accordingly, unless indicated to the contrary, the numerical values and parameters described herein are approximate values which are capable of being changed according to the desired purpose as required.

For the purposes of the present invention, the term "keratin materials" is intended to cover human skin, mucous membranes such as the lips. Facial skin is most particularly considered according to the present invention.

All percentages in the present invention refer to weight percentage, unless otherwise specified.

According to the first aspect, the present invention provides a composition for caring for keratin materials in the form of an oil-in-water cream comprising:

(i) from 3% to 10.5% by weight of at least one cosmetic active compound of formula (I), relative to the total weight of the composition:

(I)

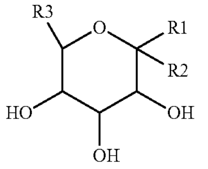

wherein R1, R2 and R3 are, independently from each other, selected from H, —OH, —$CH_2OH$ and —$CH_2CH(OH)CH_3$;

(ii) at least one water-soluble or water-dispersible copolymer derived from 2-acrylamidomethyl propanesulfonic acid and a nonionic water-soluble comonomer (AMPS copolymer);

(iii) at least one silicone compound; and (iv) ethanol.

Cosmetic Active Compounds of Formula (I)

According to the first aspect, the composition of the present invention comprises at least one cosmetic active compound of formula (I):

(I)

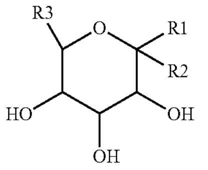

wherein R1, R2 and R3 are, independently from each other, selected from H, —OH, —$CH_2OH$ and —$CH_2CH(OH)CH_3$.

In some embodiments, the composition according to the present invention comprises hydroxypropyl tetrahydropyran triol (proxylane) as a cosmetic active compound of formula (I), wherein R1 is —$CH_2CH(OH)CH_3$, R2 and R3 are H, i.e., the compound of the following formula:

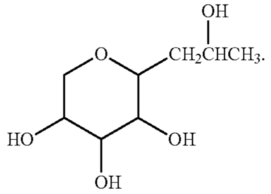

proxylane

In some embodiments, the composition according to the present invention comprises mannose as a cosmetic active compound of formula (I), wherein R1 is —$CH_2OH$, R2 is H, and R3 is —OH, i.e., the compound of the following formula:

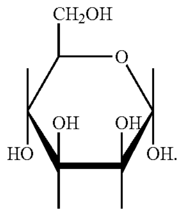

mannose

In some embodiments, the composition according to the present invention comprises glucose as a cosmetic active compound of formula (I), wherein R1 is —$CH_2OH$, R2 is H, and R3 is —OH, i.e., the compound of the following formula:

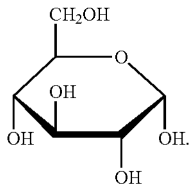

glucose

In some embodiments, the composition according to the present invention comprises galactose as a cosmetic active compound of formula (I), wherein R1 is —$CH_2OH$, R2 is H, and R3 is —OH, i.e., the compound of the following formula:

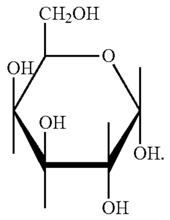

galactose

In some embodiments, the composition according to the present invention comprises fructose as a cosmetic active compound of formula (I), wherein R1 is —$CH_2OH$, R2 is —OH, and R3 is H, i.e., the compound of the following formula:

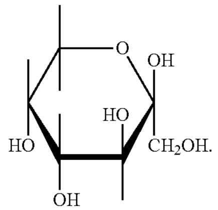

fructose

In some preferred embodiments, the cosmetic active compound of formula (I) is selected from proxylane, mannose, glucose, galactose, fructose and mixture thereof.

Commercial products of proxylane include that sold under the tradename of MEXORYL SCN by the company CHIMEX (NOVEAL), which comprises 35% by weight of proxylane.

Advantageously, the cosmetic active compound of formula (I) is present in the composition in an amount ranging from 3% to 8.75% by weight, preferably from 3.15% to 4.2% by weight, relative to the total weight of the composition.

AMPS Copolymer

According to the first aspect, the composition of the present invention comprises at least one water-soluble or water-dispersible copolymer derived from 2-acrylamidomethyl propanesulfonic acid and a nonionic water-soluble comonomer (AMPS copolymer).

The term “water-soluble or water-dispersible” means polymers which, when introduced into an aqueous phase at 25° C., to a mass concentration equal to 1%, make it possible to obtain a macroscopically homogeneous and transparent solution, i.e. a solution that has a maximum light transmittance value, at a wavelength equal to 500 nm, through a sample 1 cm thick, of at least 60% and preferably of at least 70%.

The AMPS copolymers useful in accordance with the present invention are crosslinked or non-crosslinked copolymers comprising at least the acrylamido-2-methylpropanesulfonic acid monomer, in a form partially or totally neutralized with a mineral base such as ammonia, sodium hydroxide or potassium hydroxide.

They are preferably totally neutralized or virtually totally neutralized, i.e. at least 90% neutralized.

When the polymers are crosslinked, the crosslinking agents may be chosen from the polyolefinically unsaturated compounds commonly used for the crosslinking of polymers obtained by free-radical polymerization.

Examples of crosslinking agents that may be mentioned include divinylbenzene, diallyl ether, dipropylene glycol diallyl ether, polyglycol diallyl ethers, triethylene glycol divinyl ether, hydroquinone diallyl ether, ethylene glycol or tetraethylene glycol di(meth)acrylate, trimethylolpropane triacrylate, methylenebisacrylamide, methylenebismethacrylamide, triallylamine, triallyl cyanurate, diallyl maleate, tetraallylethylenediamine, tetraallyloxyethane, trimethylolpropane diallyl ether, allyl (meth)acrylate, allylic ethers of alcohols of the sugar series, or other allylic or vinyl ethers of polyfunctional alcohols, and also allylic esters of phosphoric and/or vinylphosphonic acid derivatives, or mixtures of these compounds.

According to one embodiment of the present invention, the crosslinking agent is chosen from methylenebis-acrylamide, allyl methacrylate and trimethylolpropane triacrylate (TMPTA). The degree of crosslinking generally ranges from 0.01 mol % to 10 mol % and more particularly from 0.2 mol % to 2 mol % relative to the polymer.

The water-soluble or water-dispersible AMPS copolymers according to the present invention contain a nonionic water-soluble comonomer.

Among the nonionic water-soluble comonomers, examples that may be mentioned include:

- (meth)acrylamide,
- N-vinylacetamide and N-methyl-N-vinylacetamide,
- N-vinylformamide and N-methyl-N-vinylformamide,
- maleic anhydride,
- vinylamine,
- N-vinyllactams comprising a cyclic alkyl group containing 4 to 9 carbon atoms, such as N-vinylpyrrolidone, N-butyrolactam and N-vinylcaprolactam,
- vinyl alcohol of formula $CH_2{=}CHOH$,
- the water-soluble vinyl monomers of formula (III) below:

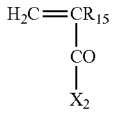

(III)

in which:

$R_{15}$ is chosen from H, $—CH_3$, $—C_2H_5$ and $—C_3H_7$, $X_2$ is chosen from alkyl ethers of $—OR_{16}$ type in which $R_{16}$ is a linear or branched, saturated or unsaturated hydrocarbon-based radical containing from 1 to 6 carbons, optionally substituted with a halogen atom (iodine, bromine, chlorine or fluorine); a hydroxyl group (—OH); ether.

Mention is made, for example, of glycidyl (meth)acrylate, hydroxyethyl (meth)acrylate, and (meth)acrylates of ethylene glycol or of diethylene glycol.

The water-soluble or water-dispersible AMPS copolymers of the present invention preferably have a molar mass ranging from 50 000 g/mol to 10 000 000 g/mol, preferably from 80 000 g/mol to 8 000 000 g/mol and even more preferably from 100 000 g/mol to 7 000 000 g/mol.

Examples of water-soluble or water-dispersible AMPS copolymers in accordance with the present invention that may be mentioned include:

- copolymers of AMPS and of vinylpyrrolidone or of vinylformamide, optionally partially or totally neutralized with a mineral base such as ammonia, sodium hydroxide or potassium hydroxide, such as the copolymer used in the commercial product sold under the name Aristoflex AVC by the company Clariant (CTFA name: Ammonium Acryloyldimethyltaurate/VP Copolymer);
- copolymers of AMPS and of hydroxyethyl acrylate, for instance AMPS/hydroxyethyl acrylate copolymer, such as the copolymer used in the commercial product sold under the name EMT 10 by the company SEPPIC (CTFA name: Hydroxyethyl acrylate/Sodium Acryloyldimethyltaurate copolymer).

Preferably, the AMPS copolymer is selected from copolymers of AMPS and of vinylpyrrolidone or of vinylformamide, optionally partially or totally neutralized with a mineral base such as ammonia, sodium hydroxide or potassium hydroxide.

Advantageously, the AMPS copolymer is present in the composition in an amount ranging from 0.3% to 3% by weight, preferably from 0.5% to 2% by weight, more preferably from 1% to 1.5% by weight, relative to the total weight of the composition.

Silicone Compounds

According to the first aspect, the composition of the present invention comprises at least one silicone compound.

Exemplary silicones include cyclic silicones, such as those having 3 to 6, or 3 to 4 or 3 to 5, (or any of 3, 4, 5, or 6) Si—O groups in the cyclic backbone chain (e.g., siloxanes). Exemplary cyclic silicones include, without limitation, cyclomethicone, cyclotetrasiloxane, cyclopentasiloxane (e.g., Cyclomethicone 5-NF), cyclohexasiloxane and a mixture of cyclohexasiloxane and cyclopenasiloxane (e.g., DOW CORNING 246 Fluid (d6+d5)).

Exemplary silicones also include silicones having side groups or side chains.

In some embodiments, the side groups are hydrophobic. In some embodiments, the side groups are straight chained, while in other embodiments the side groups are branched. Exemplary side chains include those having 1 to 6, or 2 to 6, or 3 to 6 or 3 to 6 or 5 to 6 carbons or heteroatoms (e.g., O, S, or N) (or any combination thereof). Exemplary linear side chains include, methyl, ethyl, propyl, butyl, pentyl, and hexyl. Exemplary branched side chains include, without limitation, isopropyl, isobutyl, and tert-butyl. In one non-limiting embodiment, the branched side chain is —O—Si$(CH_3)_3$.

Preferably, the silicone compound is selected from C12-C22 alkyl or alkoxy dimethicones, C6-C10 alkyl or alkoxyl methicone, and mixtures thereof.

More preferably, the silicone compound is selected from C16-C18 alkyl or alkoxy dimethicones, C6-C10 alkyl or alkoxyl methicone, and mixtures thereof.

Most preferably, the silicone compound is selected from stearyl dimethicone, cetyl dimethicone, caprylyl methicone, the structures of which are as follows:

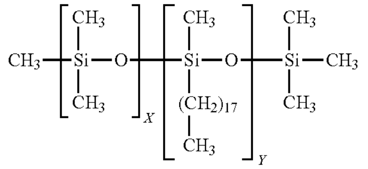

stearyl dimethicone

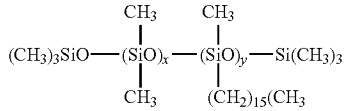

cetyl dimethicone

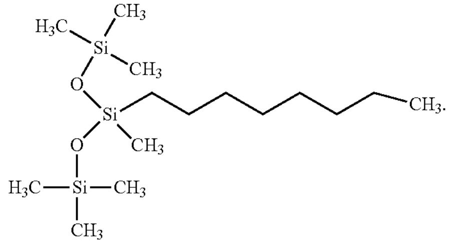

caprylyl methicone

As commercial product of stearyl dimethicone, mention can be made of that sold under the tradename ABIL WAX 9800 by the company EVONIK GOLDSCHMIDT.

As commercial product of caprylyl methicone, mention can be made of that sold under the tradename DOW CORNING FZ-3196 by the company DOW CORNING (DOW CHEMICAL).

Advantageously, the silicone compound is present in the composition in an amount ranging from 0.05% to 6% by weight, preferably from 0.5% to 5% by weight, more preferably from 2% to 4% by weight, relative to the total weight of the composition.

Aqueous Phase

As an oil-in-water cream, the cosmetic composition of the present invention comprises a continuous aqueous phase.

Advantageously, said aqueous phase is present in an amount ranging from 50% to 95% by weight, preferably from 55% to 90% by weight, and even more preferably from 60% to 85% by weight of the total weight of the composition.

Said aqueous phase comprises water and ethanol.

Advantageously, water is present in the composition of the present invention in an amount ranging from 20% to 80% by weight, preferably from 30% to 75% by weight, relative to the total weight of the composition.

Advantageously, ethanol is present in the composition of the present invention in an amount ranging from 0.5% to 20% by weight, preferably from 1% to 15% by weight, more preferably from 2% to 5% by weight, relative to the total weight of the composition.

Preferably, the continuous aqueous phase comprises an additional organic solvent miscible with water (at room temperature 25° C.) such as glycol and polyols having from 2 to 20 carbon atoms, preferably from 2 to 10 carbon atoms, and preferentially having from 2 to 6 carbon atoms, such as glycerin, propylene glycol, butylene glycol, pentylene glycol, hexylene glycol, caprylyl glycol, dipropylene glycol, diethylene glycol; and mixtures thereof, so as to provide a hydration effect.

Preferably, the continuous aqueous phase of the composition of the present invention comprises water, ethanol, butylene glycol and glycerin.

Oily Phase

As an oil-in-water cream, the composition of the present invention comprises at least one dispersed oily phase.

Advantageously, the oily phase is present in an amount ranging from 1% to 40% by weight, preferably from 2% to 30% by weight, more preferably from 3% to 20% by weight, relative to the total weight of the composition of the present invention.

Said oily phase preferably comprises at least one additional oil besides the silicone compound mentioned above. The additional oil can be volatile or non-volatile.

The term "oil" means a water-immiscible non-aqueous compound that is liquid at room temperature (25° C.) and at atmospheric pressure (760 mmHg).

The term "non-volatile oil" means an oil that may remain on keratin materials at room temperature and atmospheric pressure for at least several hours and that especially has a vapour pressure of less than $10^{-3}$ mmHg (0.13 Pa). A non-volatile oil may also be defined as having an evaporation rate such that, under the conditions defined previously, the amount evaporated after 30 minutes is less than 0.07 $mg/cm^2$.

These oils may be of plant, mineral or synthetic origin.

Said additional oil can be selected from hydrocarbonated or fluorinated oils.

The term "hydrocarbon-based oil" or "hydrocarbonated oil" means an oil formed essentially from, or even constituted by, carbon and hydrogen atoms, and optionally 0 and N atoms, and free of Si and F heteroatoms. Such oil can contain alcohol, ester, ether, carboxylic acid, amine and/or amide groups.

The term "fluorinated oil" means an oil containing at least one fluorine atom.

Preferably, the oily phase comprises an oil selected from coconut oil, coco-caprylate/caprate, squalane, and mixture thereof, to bring moisture effect, and to obtain a good balance between consistency and spreadability.

Additional Cosmetic Active Ingredients

The composition of the present invention may comprise an additional cosmetic active ingredient in addition to the cosmetic active compound of formula (I) as defined previously.

As examples of cosmetic active ingredient, mention can be made of moisturizing agents such as protein hydrolysates; natural extracts; vitamins such as vitamin A (retinol), vitamin E (tocopherol), vitamin C (ascorbic acid), vitamin B5 (panthenol), vitamin B3 (niacinamide), and derivatives of said vitamins (in particular esters) and mixtures thereof; urea; caffeine; salicylic acid and derivatives thereof; alpha-hydroxyacids such as lactic acid or glycolic acid and derivatives thereof; retinoids such as carotenoids and derivatives of vitamin A; sunscreens; extracts from algae, fungi, plants, yeasts and bacteria; enzymes; tightening agents; agents acting on the microcirculation, and mixtures thereof.

It is easy for the skilled in the art to adjust the amount of the additional cosmetic active ingredient based on the final use of the composition according to the present invention.

Additional Adjuvants or Additives

The composition of the present invention may comprise may also contain conventional cosmetic adjuvants or additives, for instance fragrances, chelating agents (for example, tetrasodium glutamate diacetate and disodium EDTA), preserving agents (for example, chlorphenesin and phenoxy ethanol) and bactericides, emulsifier, co-emulsifier (for example, hydrogenated lecithin), additional thickeners (such as acrylates/C10-30 alkyl acrylate crosspolymer), pH regulators (for example, triethanolamine, citric acid and sodium hydroxide), fillers (for examples aluminum starch octenylsuccinate and polymethiylsisesquioxane) and mixtures thereof.

In some embodiments, the composition of the present invention comprises a filler selected from aluminum starch octenylsuccinate, polymethiylsisesquioxane, a mixture thereof to further decrease the stickiness.

The skilled in the art can select the amount of the additional adjuvants or additive so as not to adversely impact the final use of the composition according to the present invention.

According to a particularly preferred embodiment, the present invention provides a composition for caring for keratin materials in the form of an oil-in-water cream comprising, relative to the total weight of the composition:

(i) from 3.15% to 4.2% by weight of at least one cosmetic active compound selected from proxylane, mannose, glucose, galactose, fructose and mixture thereof;

(ii) from 1% to 1.5% by weight of at least one water-soluble or water-dispersible copolymer of AMPS and of vinylpyrrolidone or of vinylformamide, optionally partially or totally neutralized with a mineral base such as ammonia, sodium hydroxide or potassium hydroxide;

(iii) from 2% to 4% by weight of at least one silicone compound selected from C16-C18 alkyl or alkoxy dimethicones, C6-C10 alkyl or alkoxyl methicone, and mixtures thereof; and (iv) from 2% to 5% by weight of ethanol.

Galenic Form and Method

The composition of the present invention is in the form of a cream.

Preferably, the composition according to the present invention has a viscosity ranging from 37 to 70 UD (Deviation Units), measured at 25° C. using a Rheomat 180 viscometer equipped with a spindle M3 rotating at 200 rpm.

The composition of the present invention can be used for caring for keratin materials.

According to the second aspect, the present invention provides a non-therapeutic method for caring for keratin materials, comprising applying the composition according to the first aspect of the present invention to the keratin materials.

In some embodiments, the present invention provides a non-therapeutic method for antiaging of keratin materials, comprising applying the composition according to the first aspect of the present invention to the keratin materials.

The following examples serve to illustrate the present invention without, however, being limiting in nature.

EXAMPLES

Main raw materials used, trade names and supplier thereof are listed in Table 1.

TABLE 1

| INCI Name | Trade Name | Supplier |
|---|---|---|
| GLYCERIN | GLICENAT ® GC K MB | OXITENO |
| BUTYLENE GLYCOL | 1,3 BUTYLENE GLYCOL | ALZO |
| PHENOXYETHANOL | HUNTSMAN (INDORAMA) | GLYSOLV EPHL |
| TETRASODIUM GLUTAMATE DIACETATE | DISSOLVINE ® GL-47-S | AKZO NOBEL (NOURYON) |
| HYDROGENATED LECITHIN | NIKKOL LECINOL S 10 | NIKKO |
| CHLORPHENESIN | MACROCIDE-OL | MACROCARE |
| *COCOS NUCIFERA* (COCONUT) OIL | NEUTRESCA 51-25 | AARHUSKARLSHAMN |
| CAPRYLYL METHICONE | DOW CORNING FZ-3196 | DOW CORNING (DOW CHEMICAL) |
| STEARYL DIMETHICONE | ABIL ® WAX 9800 | EVONIK GOLDSCHMIDT |
| *BUTYROSPERMUM PARKII* (SHEA) BUTTER | LIPEX ® 102 | AARHUSKARLSHAMN |
| ACRYLATES/C10-30 ALKYL ACRYLATE CROSSPOLYMER | PEMULEN TR-1 POLYMER | LUBRIZOL |

TABLE 1-continued

| INCI Name | Trade Name | Supplier |
|---|---|---|
| TRIETHANOLAMINE | TRIETANOLAMINA 99 | OXITENO |
| AMMONIUM ACRYLOYLDIMETHYLTAURATE/VP COPOLYMER | ARISTOFLEX AVC | CLARIANT |
| AMMONIUM POLYACRYLOYLDIMETHYL TAURATE | HOSTACERIN AMPS | CLARIANT |
| HYDROXYPROPYL TETRAHYDROPYRANTRIOL | MEXORYL SCN | CHIMEX (NOVEAL) |
| ETHANOL | ABSOLUTE ETHANOL | ANHUI ANTE FOOD |

Example 1

Compositions of comparative formulas (Comp.) 1-4 and inventive formula (Inv.) 1-3 were prepared according to the amounts given in Table 2. The amounts are given in % by weight of active ingredient relative to the total weight of the composition.

TABLE 2

| Components | Inv. 1 | Inv. 2 | Inv. 3 | Comp. 1 | Comp. 2 | Comp. 3 | Comp. 4 |
|---|---|---|---|---|---|---|---|
| | wt. % | | | | | | |
| WATER | QS100 | QS100 | QS100 | QS100 | QS100 | QS100 | QS100 |
| GLYCERIN | 5 | 5 | 5 | 5 | 5 | 5 | 5 |
| BUTYLENE GLYCOL | 2 | 2 | 2 | 2 | 2 | 2 | 2 |
| PHENOXYETHANOL | 0.5 | 0.5 | 0.5 | 0.5 | 0.5 | 0.5 | 0.5 |
| TETRASODIUM GLUTAMATE DIACETATE | 0.1 | 0.1 | 0.1 | 0.1 | 0.1 | 0.1 | 0.1 |
| HYDROGENATED LECITHIN | 0.6 | 0.6 | 0.6 | 0.6 | 0.6 | 0.6 | 0.6 |
| CHLORPHENESIN | 0.2 | 0.2 | 0.2 | 0.2 | 0.2 | 0.2 | 0.2 |
| *COCOS NUCIFERA* (COCONUT) OIL | 1 | 1 | 1 | 1 | 1 | 1 | 1 |
| CAPRYLYL METHICONE | 3 | — | 3.3 | 3 | 3 | 3 | 3 |
| STEARYL DIMETHICONE | 0.3 | 3.3 | — | 0.3 | 0.3 | 0.3 | 0.3 |
| *BUTYROSPERMUM PARKII* (SHEA) BUTTER | 0.5 | 0.5 | 0.5 | 0.5 | 0.5 | 0.5 | 0.5 |
| TRIETHANOLAMINE | Adjusting pH to 5-6 | | | | | | |
| AMMONIUM ACRYLOYLDIMETHYLTAURATE/ VP COPOLYMER | 1.2 | 1.2 | 1.2 | 0 | 1.2 | — | — |
| AMMONIUM POLYACRYLOYLDIMETHYL TAURATE | — | — | — | — | — | 1.2 | — |
| ACRYLATES/C10-C30 ALKYL ACRYLATE CROSSPOLYMER | — | — | — | — | — | — | 1.2 |
| HYDROXYPROPYL TETRAHYDROPYRANTRIOL | 3.15 | 3.15 | 3.15 | 3.15 | 3.15 | 3.15 | 3.15 |
| ETHANOL | 3 | 3 | 3 | 3 | 0 | 3 | 3 |

Composition of comparative example 1 does not comprise any AMPS copolymer.

Composition of comparative example 2 does not comprise ethanol.

Composition of comparative example 3 comprises ammonium polyacryloyldimethyl taurate, instead of AMPS copolymer according to the present invention.

Composition of comparative example 4 comprises acrylates/C10-C30 alkyl acrylate crosspolymer, instead of AMPS copolymer according to the present invention.

Preparation Process:

The compositions listed above were prepared as follows, taking the composition of invention formula 1 as an example:

1) Mixing COCOS NUCIFERA (COCONUT) OIL, SHEAR BUTTER, CAPRYLYL METHICONE and STEARYL DIMETHICONE to obtain an oily phase, and mixing WATER, GLYCERIN, BUTYLENE GLYCOL, PHENOXYETHANOL, TETRASODIUM GLUTAMATE DIACETATE, and HYDROGENATED LECITHIN to obtain an aqueous phase;

2) Heating the oily phase and the aqueous phase to 75° C.;

3) Mixing the oily phase and the aqueous phase to obtain a mixture, and homogenizing the mixture with high shearing speed;

4) Then adding polymer (AMMONIUM ACRYLOYLDIMETHYLTAURATE/VP COPOLYMER) to the mixture and cooling it down to room temperature with gentle stirring after polymer well jellified in water;

5) Adding HYDROXYPROPYL TETRAHYDROPYRANTRIOL and ETHANOL at room temperature and stirring to disperse homogeneously;

6) Adjusting pH to 5-6 by adding appropriate amount of TRIETHANOLAMINE.

Evaluation

The viscosity of each composition obtained was measured at 25° C. using a Rheomat 180 viscometer equipped with a spindle M3 rotating at 200 rpm.

The stability of each composition obtained was evaluated by maintaining the composition at 4° C., room temperature (25° C.), or 45° C. and observing with naked eyes to check whether the composition will be layered within 48 hours after stirring. It will be evaluated as stable if the composition tested is not layered under all of 4° C., room temperature (25° C.), and 45° C. within 48 hours after stirring, otherwise, it will be evaluated as unstable.

The stickiness of each composition prepared above was evaluated as follows.

5 skincare formulation scientists applied 50 µl of the composition tested on an area of 6.3 cm×6.3 cm of arm skin with two washed fingers. Then the stickiness was scored during application and after application according to the following standards and averaged:

1=not sticky,

2=just right stickiness for a facial cream,

3=very sticky.

The spreadability was scored during application according to the following standards and averaged:

1=very easy to spread,

2=not difficult and not very easy to spread,

3=difficult to spread.

In addition, the aspect of each composition obtained was observed with naked eyes.

The results of the viscosity, stability, stickiness, spreadability and aspect of the compositions according to comparative formula and inventive formulas were listed in Table 3.

TABLE 3

| Properties | Inv. 1 | Inv. 2 | Inv. 3 | Comp. 1 | Comp. 2 | Comp. 3 | Comp. 4 |
|---|---|---|---|---|---|---|---|
| Viscosity (UD) | 39 | 40.4 | 39.2 | NA | 40.2 | 58.4 | 60.6 |
| Stability | | Stable | | Unstable | | Stable | |
| Stickiness | 1.3 | 1.3 | 1.3 | NA | 1.9 | 1.3 | 1.5 |
| Spreadability | 1 | 1 | 1 | NA | 1 | 2 | 3 |
| Aspect | Smooth and fine texture | | | NA | Smooth and fine texture | | Not smooth and trembling aspect |

NA stands for "not tested".

The compositions of invention formulas 1-3 have a smooth and fine texture as a cream and have a good spreadability. The compositions of invention formulas 1-3 can deliver an antiaging effect to the skin without sticky sensory. Furthermore, the composition of invention formulas 1-3 is stable at 4° C., room temperature (25° C.), and 45° C.

The invention claimed is:

1. A composition for caring for keratin materials, comprising:

(1) from 3% to 10.5% by weight of a compound of formula (I), relative to the total weight of the composition:

(I)

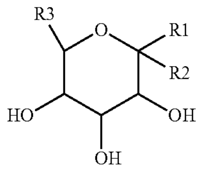

wherein R1 is $CH_2CH(OH)CH_3$, and

R2 and R3 are H or OH;

(ii) at least one water-soluble or water-dispersible copolymer derived from 2-acrylamidomethyl propanesulfonic acid (AMPS) and a nonionic water-soluble comonomer;

(iii) at least one silicone compound; and (iv) ethanol, wherein the composition is in the form of an oil-in-water cream having a continuous aqueous phase.

2. The composition according to claim 1, wherein the composition further comprises a compound selected from the group consisting of mannose, glucose, galactose, fructose and mixtures thereof.

3. The composition according to claim 1, wherein the compound of formula (I) is present in an amount ranging from 3% to 8.75% by weight relative to the total weight of the composition.

4. The composition according to claim 1, wherein the nonionic water-soluble comonomer of the water-soluble or water-dispersible copolymer is selected from the group consisting of (meth) acrylamide, N-vinylacetamide, N-methyl-N-vinylacetamide, N-vinylformamide, N-methyl-N-vinylformamide, maleic anhydride, vinylamine, N-vinyllactams comprising a cyclic alkyl group containing 4 to 9 carbon atoms, vinyl alcohol of formula $CH_2{=}CHOH$, and water-soluble vinyl monomers of formula (III):

(III)

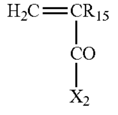

$R_{15}$ is H, $—CH_3$, $—C_2H_5$ or $—C_3H_7$, $X_2$ is $OR_{16}$, wherein $R_{16}$ is a linear or branched, saturated or unsaturated hydrocarbon-based radical containing from 1 to 6 carbons, optionally substituted with a halogen atom, a hydroxyl group, or an ether.

5. The composition according to claim 4, wherein the water-soluble or water-dispersible copolymer is selected from copolymers of AMPS with vinylpyrrolidone or vinylformamide, optionally partially or totally neutralized with a mineral base selected from the group consisting of ammonia, sodium hydroxide and potassium hydroxide.

6. The composition according to claim 1, wherein the water-soluble or water-dispersible copolymer is present in amount ranging from 0.3% to 3% by weight relative to the total weight of the composition.

7. The composition according to claim 1, wherein the silicone compound is selected from C12-C22 alkyl or alkoxy dimethicones, C6-C10 alkyl or alkoxyl methicone, or mixtures thereof.

8. The composition according to claim 1, wherein the silicone compound is present in an amount ranging from 0.05% to 6% by weight relative to the total weight of the composition.

9. The composition according to claim 1, wherein the continuous aqueous phase of the composition comprises water, ethanol, butylene glycol and glycerin.

10. The composition according to claim 1, wherein ethanol is present in an amount ranging from 0.5% to 20% by weight, relative to the total weight of the composition.

11. The composition according to claim 1, wherein the composition comprises, relative to the total weight of the composition:

(i) from 3.15% to 4.2% by weight of the compound of formula (I);

(ii) from 1% to 1.5% by weight of at least one water-soluble or water-dispersible copolymer of AMPS with vinylpyrrolidone or vinylformamide, optionally partially or totally neutralized with a mineral base selected from the group consisting of ammonia, sodium hydroxide and potassium hydroxide;

(iii) from 2% to 4% by weight of at least one silicone compound selected from the group consisting of C12-C22 alkyl or alkoxy dimethicones, C6-C10 alkyl or alkoxyl methicone, and mixtures thereof; and (iv) from 2% to 5% by weight of ethanol.

12. A method for caring for keratin materials in a human, comprising applying the composition according to claim 1 to the keratin materials.

13. The composition according to claim 1, wherein the silicone compound is selected from the group consisting of stearyl dimethicone, cetyl dimethicone and caprylyl methicone.

* * * * *